United States Patent [19]

Knifton

[11] 4,308,403

[45] Dec. 29, 1981

[54] PROCESS FOR PREPARING GLYCOL ETHERS

[75] Inventor: John F. Knifton, Austin, Tex.

[73] Assignee: Texaco Inc., White Plains, N.Y.

[21] Appl. No.: 186,934

[22] Filed: Sep. 12, 1980

[51] Int. Cl.$^3$ .......................................... C07C 111/01
[52] U.S. Cl. .................................... 568/678; 568/672
[58] Field of Search ................................ 568/672, 678

[56] References Cited

U.S. PATENT DOCUMENTS 4,071,568  1/1978  Onoda et al. ..................... 568/678

Primary Examiner—Howard T. Mars
Attorney, Agent, or Firm—Carl G. Ries; Robert A. Kulason; Walter D. Hunter

[57] ABSTRACT

This invention pertains to the production of glycol monoalkyl ethers and dialkyl ethers by reaction of an aldehyde, and an alcohol with carbon monoxide and hydrogen in the presence of a catalyst comprising a cobalt-containing compound and a Group VIB donor ligand.

22 Claims, No Drawings

PROCESS FOR PREPARING GLYCOL ETHERS

BACKGROUND OF THE INVENTION

1. Field of the Invention

This invention relates to a process for the preparation of glycol monoalkyl- and dialkyl-ethers by the reaction of synthesis gas, an aldehyde and an alcohol using a specific catalyst system.

2. Prior Art

There is an ever increasing need for a wide variety of glycol monoalkyl- and dialkyl-ethers of differing carbon numbers and structures which have become important present articles of commerce. Such ethers are employed in a wide variety of applications as solvents, reaction media, etc. In conventional processes an olefin oxide such as ethylene oxide is first prepared from an olefin and reacted with suitable alcohol. Since the cost of materials derived from petroleum solutions has been rising rapidly, research efforts are now being made to find a new process for producing these glycol ethers which does not utilize an olefin as a starting material. One of the newer methods for the preparation of glycol monoalkylethers, in which an acetal is reacted with carbon monoxide and hydrogen in the presence of a cobalt carbonyl catalyst in the presence of a cobalt carbonyl catalyst, is described in German Pat. Nos. 875,802 and 890,945. This process suffers from several disadvantages including a low selectivity of the glycol ether and decomposition of the carbonyl catalyst during recovery of the product from the raction mixture.

In U.S. Pat. No. 4,071,568 a process for making glycol monoethers is disclosed in which the catalyst utilized is cobalt carbonyl combined with a trivalent organic phosphorus compound such as tri-n-butyl phosphine which is reported to give better selectivity.

One of the objects of this invention is to provide a novel process for preparing glycol monoalkyl- and dialkyl-ethers by means of a unique catalyst system in which the feedstock utilized comprises an aldehyde, an alcohol and synthesis gas.

Another object of this invention is to provide a process for producing glycol alkylethers in high yield.

SUMMARY OF THE INVENTION

In this invention glycol monoalkylethers and dialkylethers are prepared by reaction of an aldehyde, a monohydric alcohol and synthesis gas in the presence of a catalyst comprising a cobalt-containing compound and at least one Group VIB donor ligand at superatmospheric pressures.

The process of this invention is shown in the following equations where for purposes of illustration the reaction of carbon monoxide, hydrogen, formaldehyde and an alcohol is shown:

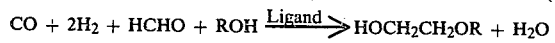

(1)

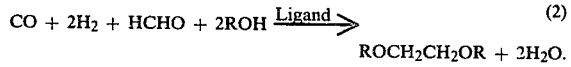

(2)

A wide variety of alcohols and aldehydes may be employed in the process of this invention.

A high degree of selectivity is exhibited by the reaction of this invention. For example, when formaldehyde and butanol are reacted with carbon monoxide and hydrogen in the process of this invention combined yields of ethylene glycol monobutyl- and dibutyl-ethers as high as 64 percent, based on the formaldehyde charged to the reactor have been obtained.

DETAILED DESCRIPTION OF THE INVENTION

This invention relates to a process for preparing monoalkylethers and dialkylethers by a process which comprises reacting a mixture of hydrogen, carbon monoxide, an aldehyde of the formula:

wherein R is selected from the group consisting of hydrogen and alkyl of from 1 to 10 carbon atoms and an alcohol of the formula:

wherein R' is alkyl of from 1 to 10 carbon atoms, in the presence of a catalyst comprising a cobalt-containing compound and at least one Group VIB donor ligand at superatmospheric pressures of 500 psi or greater until substantial formation of the said glycol monoalkylethers and dialkylethers has been achieved and recovering the said ethers from the reaction mixture.

In carrying out the reaction of this invention selectively to produce high yields of the desired glycol monoalkylethers and dialkylethers it is necessary to supply sufficient carbon monoxide, hydrogen, aldehyde and alcohol to at least satisfy the stoichiometry of equations (1) and (2) above although an excess of one or more of the reactants over the stoichiometric amounts may be present.

Catalysts that are suitable for use in the practice of this invention contain cobalt. The cobalt-containing compounds may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise cobalt in complex combination with the ligand and with carbon monoxide and hydrogen. The most effective catalyst is achieved where the cobalt hydrocarbonyl species is solubilized in the alcohol co-reactant employed.

The cobalt-containing catalyst precursors may take many different forms. For instance, the cobalt may be added to the reaction mixture in an oxide form, as in the case of, for example, cobalt(II) oxide (CoO) or cobalt (II,III) oxide (Co$_3$O$_4$). Alternatively, it may be added as the salt of a mineral acid, as in the case of cobalt(II) chloride (CoCl$_2$), cobalt(II) chloride hydrate (CoCl$_2$·6H$_2$O), cobalt(II) bromide (CoBr$_2$), cobalt(II) iodide (CoI$_2$) and cobalt(II) nitrate hydrate (Co(NO$_3$)$_2$.6H$_2$O), etc., or as the salt of a suitable organic carboxylic acid, for example, cobalt(II) formate, cobalt(II) acetate, cobalt(II) propionate, cobalt naphthenate, cobalt acetylacetonate, etc. The cobalt may also be added to the reaction zone as a carbonyl or hydrocarbonyl derivative. Here, suitable examples include dicobalt octacarbonyl (Co$_2$(CO)$_8$), cobalt hydrocarbonyl (HCo(CO)$_4$) and substituted carbonyl species such as the triphenyl phosphine cobalt tricarbonyl dimer, etc.

Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(II) chloride, cobalt acetylacetonate, cobalt(II) acetate, cobalt(II) propionate, and dicobalt octacarbonyl.

In the process of this invention the reaction is conducted in the presence of a catalyst comprising a cobalt-containing compound and a Group VIB donor ligand as set out in the Periodic Table as shown on page 125 of Mellor's, Modern Inorganic Chemistry, sixth edition, 1967. The cobalt-containing compound employed may be a cobalt carbonyl or a compound capable of forming a cobalt carbonyl under reaction conditions. The catalyst may be introduced into the raction system as a preformed complex by combining the cobalt-containing compound with the Group VIB donor ligand to form a complex which is then introduced into the reaction mixture. Alternatively, the Group VIB ligand and the cobalt-containing compound may be separately introduced into the reaction system where the complex is formed under reaction conditions.

The Group VIB donor ligand which may be utilized with the cobalt-containing compounds in this process include compounds of the formula:

$$R''-Y-R'''$$

where Y is selected from the group consisting of selenium, sulfur and oxygen and R'' and R''' are independently selected from the group consisting of alkyl of from 1 to 8 carbon atoms as exemplified by methyl, ethyl, propyl, butyl, pentyl, heptyl, octyl and isomers thereof, aryl from 6 to 9 inclusive carbon atoms such as phenyl, tolyl and xylyl as well as substituted alkyl or aryl where the substituents are alkoxy, halo and thio groups. Examples of suitable group VIB donor ligands include sulphides such as ditolylsulphide, di-n-butylsulphide, butyl phenyl sulphide, thioanisole, di-tert-butylsulphide, tert-butyl methyl sulphide, diphenylsulphide, bis(2-cyanoethyl)sulphide, 1,2-bis(phenylthio)ethane, 2-chlorethyl phenyl sulphide, chloromethyl phenyl sulphide, p-chlorophenyl methyl sulphide, ethyl phenyl sulphide, and ethyl thioethanol. Also suitable as ligands are the corresponding selenides and ethers, examples include diphenylselenide, diphenyl oxide, di-n-butyl selenide, dibutyl ether, di-n-octylether, butyl phenyl ether and n-octyl selenide.

A preferred class of group VIP donor ligands includes diphenyl selenide, diphenyl sulphide, and diphenyl oxide.

The number of gram moles of the Group VIB donor ligand employed per gram atom of cobalt can be varied widely and is generally in the range of 0.1 to 100 and preferably from 0.5 to 5.

Alcohols useful as starting materials in the process of this invention have the formula:

$$R'OH$$

where R' is alkyl of from 1 to 10 carbon atoms. Suitable alcohols include methanol, ethanol, propanol, butanol, heptanol, decanol, etc. and isomers thereof.

Aldehydes which may be utilized in the process of this invention include compounds of formula:

$$RCHO$$

where R is selected from the group consisting of hydrogen and alkyl of from 1 to 10 carbon atoms as exemplified by methyl, ethyl, butyl, hexyl, nonyl, etc. and isomers thereof. Compounds capable of releasing an aldehyde under reaction conditions such as aldehyde polymers including paraformaldehyde and trioxane may be utilized in the process of this invention. The preferred aldehydes are formaldehyde and a paraformaldehyde.

The quantity of cobalt catalyst employed in the instant invention is not critical and may vary over a wide range. In general, the novel process is desirably conducted in the presence of a catalytically effective quantity of one or more of the active cobalt species together with one or more of the Group VIB donor ligands which gives the desired products in reasonable yields. The reaction proceeds when employing as little as about $1\times10^{-6}$ weight percent and even lesser amounts of cobalt, basis the total weight of the reaction mixture. The upper concentration is dictated by a variety of factors including catalyst cost, partial pressures of carbon monoxide and hydrogen, operating temperature, etc. A cobalt catalyst concentration of from about $1\times10^{-5}$ to about 10 weight percent cobalt, based on the total weight of reaction mixture, is generally desirable in the practice of this invention.

The temperature range which can usefully be employed in these syntheses is a variable dependent upon other experimental factors, including the choice of the aldehyde, the alcohol, the pressure, and the concentration and choice of particular species of the cobalt-containing compound and the Group VIB donor ligand among other things. The range of operability is from about 50° to about 300° C. when superatmospheric pressures of syngas are employed. A narrower range of about 100° to about 250° C. represents the preferred temperature range.

Superatmospheric pressures of 500 psi or greater lead to substantial yields of desirable glycol ethers by the process of this invention. A preferred operating range is from about 1000 psi to about 5000 psi, although pressures above 5000 psi also provide useful yields of the desired acid. The pressures referred to here represent the total pressure generated by all the reactants, although they are substantially due to the carbon monoxide and hydrogen fractions in these examples.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether.

In all these syntheses in order to achieve a high degree of selectivity the amount of carbon monoxide, hydrogen, aldehyde and alcohol present in the reaction mixture should be sufficient to at least satisfy the stoichiometry of eq (1) or (2) depending up the desired glycol alkylether. Excess carbon monoxide and/or hydrogen or any of the reactants over the stoichiometric amounts may be present, if desired.

As far as can be determined, without limiting the invention thereby, the cobalt-catalyst one-step process disclosed herein leads primarily to the formation of glycol alkylether products. In the case then where formaldehyde and methanol are the co-reactants, the principal products are ethylene glycol monomethylether and ethylene glycol dimethylether. By-products such as water and dimethoxymethane are also detected in the liquid product fraction.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ester product, and said material may be recovered by methods well known in the art, such as distillation, fractionation, extraction and the like. A fraction rich in cobalt catalyst components may then be recycled to the reaction zone, if desired, and additional products generated.

The products have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psi).

The following examples which illustrate various embodiments of the invention are to be considered not limitative.

EXAMPLE I

To a 450 ml glass-lined pressure reactor was charged a mixture of dicobalt octacarbonyl (2 mmole Co), diphenylselenide (2 mmole) and paraformaldehyde (0.1 mole) in 37.1 g of n-butanol (0.5 mole). After flushing with nitrogen, the reactor was sealed and flushed with a gaseous mixture containing equal molar amounts of carbon monoxide and hydrogen following which it was pressured to 2700 psi with a gaseous mixture containing 2 moles of hydrogen per mole of carbon monoxide and finally heated to 160° C. with agitation. After 4 hours at 160° C. the reactor was allowed to cool, the excess gas was sampled and vented and a deep-brown liquid product (42.7 g) was recovered.

Analysis by glc of the liquid product showed the presence of:
16.8 wt % ethylene glycol monobutyl ether
1.0 wt % ethylene glycol dibutyl ether
4.5 wt % water
75.2 wt % unreacted n-butanol Estimated yield of ethylene glycol monobutyl ether (basis paraformaldehyde charged) was 61 mole percent. Total glycol monobutyl and dibutyl ether yield was 64 mole percent.

Typical off-gas samples showed the presence of:
29.79% carbon monoxide
62.1% hydrogen
5.9% carbon dioxide The glycol monobutyl ether was recovered by distillation in vacuo.

EXAMPLES 2-4

Following the general procedure of Example 1, additional catalysts and promoters were employed in Examples 2–4. Specifically:

(a) Example 2 demonstrates the effective use of diphenyl sulfide with dicobalt octacarbonyl as the catalyst.

(b) Cobalt(II) acetate and diphenyl selenide was successfully employed as the soluble catalyst in Example 3.

(c) In Example 4 glycol monobutyl and dibutylethers were prepared utilizing a 40 percent solution of formaldehyde in butanol as the source of formaldehyde.

(d) Example 5 demonstrates the effective use of diphenyl oxide with dicobalt octacarbonyl as the catalyst.

Results are summarized in Table I which follows.

TABLE I

Ethylene Glycol Alkyl Ethers From Syngas

| Example | Catalyst Composition | Alcohol | Time hr | Temp °C. | Liquid Composition[c] (Wt %) | | | | | | EGMBE[d] Yield (Mole %) |
|---|---|---|---|---|---|---|---|---|---|---|---|
| | | | | | $H_2O$ | MeOH | BuOH | EGMBE[d] | EGDBE[e] | BuOOCH | |
| 1[a] | $Co_2(CO)_8$—$SePh_2$ | BuOH | 4 | 160 | 4.5 | 0.4 | 75.2 | 16.8 | 1.0 | 0.2 | 61 |
| 2[a] | $Co_2(CO)_8$—$SPh_2$ | BuOH | 4 | 160 | 4.9 | 0.2 | 82.1 | 10.6 | 0.1 | 0.1 | 38 |
| 3[a] | $Co(OAc)_2$—$SePh_2$ | BuOH | 4 | 160 | 4.4 | 0.2 | 79.0 | 11.9 | 1.0 | 0.1 | 44 |
| 4[b] | $Co_2(CO)_8$—$SePh_2$ | BuOH | 4 | 160 | 8.7 | 1.7 | 63.0 | 11.5 | 0.3 | | 24 |
| 5[a] | $Co_2(CO)_8$—$Ph_2O$ | BuOH | 4 | 160 | 4.5 | 0.2 | 72.0 | 11.5 | | | 46 |

[a]Run Conditions: 2 mmole Co; 0.5 mole BuOH; 0.1 mole $(HCHO)_n$; Co/Se, O or S atomic ratio 1/1, $H_2/CO$ (2:1) initial pressure 2700 psi.
[b]Run Conditions: charging 0.1 mole $(HCHO)_n$ as a 40% solution in butanol (8.0g) 0.2 mole BuOH, 4 mmole Co; Co/Se atomic ratio 2/1, $H_2/CO$ (2:1); initial pressure 2700 psi.
[c]analysis by glc, Karl Fischer titration.
[d]EGMBE, ethylene glycol monobutyl ether; yield basis formaldehyde charged.
[e]EGDBE, ethylene glycol dibutyl ether.

EXAMPLE 6

Following the procedures of Example 1, to a 180 ml glass-lined pressure reactor was charged a mixture of dicobalt octacarbonyl (2 mmole Co), diphenylselenide (2 mmole) and parafromaldehyde (0.1 mole) in 16.0 g of methanol (0.5 mole). After flushing with syngas ($CO/H_2$ mixture), the reactor was pressured to 2700 psi with a gaseous mixture containing 2 moles of hydrogen per mole of carbon monoxide and heated to 200° C. with agitation.

After 4 hours at 200° C. the reactor was cooled, the excess gas sampled and vented, and the green-brown liquid product (20.7 g) was recovered.

Analysis of the liquid product (glc and Karl Fischer Titration) showed the presence of:
5.6 wt% ethylene glycol monomethyl ether
0.3 wt% ethylene glycol dimethyl ether
4.6 wt% dimethoxymethane
10.3 wt% water
73.5 wt% unreacted methanol Typical off-gas samples showed the presence of:
61% hydrogen
29% carbon monoxide
67% carbon dioxide

EXAMPLE 7

Following the general procedure of Examples 1–5 inclusive, the 450 ml glass-lined pressure reactor was charged with 0.1 mole of paraformaldehyde, dicobalt octacarbonyl (2.0 mmole Co), diphenylsulphide (2.0 mmole) and 0.5 mole of n-butanol. After flushing with syngas ($CO/H_2$ mixture), the reactor was pressurized to 2700 psi with a gaseous mixture containing 2 moles of hydrogen per mole of carbon monoxide, and heated to 160° C. with agitation. After 4 hours at temperature, the reactor was cooled and vented and the clear red liquid product recovered and analyzed by glc and Karl Fischer Titration. There were no residual solids at this state.

The product liquid was distilled in vacuo, and ethylene glycol monobutyl ether was recovered as a distillate fraction at 48°–52° C. (1 mm Hg pressure). The residual catalyst remained behind as a deep-red colored liquid (2.3 g) and this residual catalyst liquid was returned to the 450 ml glass-lined reactor by washing with additional n-butanol (0.5 mole). Fresh paraformaldehyde (0.1 mole) was also added at this stage, the reactor sealed, flushed with syngas, pressured to 2700 psi with $CO/H_2$ (1:2) and heated to 160° C. with agitation for 4 hours. In this manner the synthesis of ethylene glycol monobutyl ether was repeated successfully, and the later recovered from the crude liquid product (44.5 g) by vacuum distillation as outlined above.

The residual catalyst solution (4.8 g) from this second cycle was again returned to the reactor for further glycol ether synthesis. The yields of glycol monobutyl ether (basis paraformaldehyde charged) for this three cycle experiment are shown in Table II.

TABLE II

Ethylene Glycol Butyl Ethers From Syngas-Catalyst Recycling

| Example | Number of Catalyst Cycles | Yield of $BuOCH_2CH_2OH$ (%)$^a$ |
| --- | --- | --- |
| 7 | 1 | 45 |
|   | 2 | 46 |
|   | 3 | 47 |

What is claimed is:

1. A process for preparing glycol monoalkylethers and dialkylethers which comprises reacting a mixture of hydrogen, carbon monoxide, an aldehyde of the formula:

RCHO, wherein R is selected from the group consisting of hydrogen and alkyl of from 1 to 10 carbon atoms and an alcohol of the formula:

R'OH, wherein R' is alkyl of from 1 to 10 carbon atoms, in the presence of a catalyst comprising a cobalt-containing compound and at least one Group VIB donor ligand at superatmospheric pressures of 500 psi or greater until substantial formation of the said glycol monoalkylethers and dialkylethers has been achieved and recovering the said ethers from the reaction mixture.

2. The process of claim 1 wherein the said reaction mixture is heated at a temperature of from about 50° to about 300° C.

3. The process of claim 1 wherein the said reaction mixture is heated at a temperature of about 100° to about 250° C.

4. The process of claim 1 wherein the process is conducted at a pressure of about 1000 psi to about 5000 psi.

5. The process of claim 1 wherein the said cobalt-containing compound is selected from the group consisting of one or more oxides of cobalt, cobalt salts of a mineral acid, cobalt salts of an organic carboxylic acid and cobalt carbonyl or hydrocarbonyl derivatives.

6. The process of claim 5 wherein the said cobalt-containing compound is selected from the group consisting of cobalt oxide, cobalt chloride, cobalt iodide, cobalt nitrate, cobalt sulfate, cobalt acetate, cobalt propionate, cobalt acetylacetonate, and dicobalt octacarbonyl.

7. The process of claim 6 wherein said cobalt compound is cobalt acetate.

8. The process of claim 6 wherein said cobalt compound is dicobalt octacarbonyl.

9. The method of claim 1 wherein said aldehyde is selected from the group consisting of formaldehyde and paraformaldehyde.

10. The process of claim 9 wherein the said aldehyde is formaldehyde.

11. The process of claim 9 wherein the said aldehyde is paraformaldehyde.

12. The process of claim 1 wherein the said alcohol is selected from the group consisting of methanol, ethanol, propanol, butanol, pentanol and isomers thereof.

13. The process of claim 12 wherein the said alcohol is methanol.

14. The process of claim 12 wherein the said alcohol is ethanol.

15. The process of claim 12 wherein the said alcohol is n-butanol.

16. The process of claim 1 wherein the said Group VIB donor ligand is a compound of the formula:

R''—Y—R''', wherein Y is selected from the group consisting of selenium, sulfur and oxygen and R'' and R''' are independently selected from the group consisting of alkyl of from 1 to 8 carbon atoms and aryl of 6 to 9 carbon atoms.

17. The process of claim 16 wherein the said Group VIB donor ligand is diphenyl selenide.

18. The process of claim 16 wherein the said Group VIB donor ligand is diphenyl sulfide.

19. The process of claim 16 wherein the said Group VIB donor ligand is diphenyl oxide.

20. The process of claim 1 wherein the said aldehyde is formaldehyde, the said alcohol is n-butanol, the said cobalt-containing compound is dicobalt octacarbonyl and the said Group VIB donor ligand is diphenyl selenide.

21. The process of claim 1 wherein the said aldehyde is formaldehyde, the said alcohol is n-butanol, the said cobalt-containing compound is dicobalt octacarbonyl and the said Group VIB donor ligand is diphenyl oxide.

22. The process of claim 1 wherein the said aldehyde is formaldehyde, the said alcohol is n-butanol, the said cobalt-containing compound is dicobalt octacarbonyl and the said Group VIB donor ligand is diphenyl sulfide.

* * * * *